United States Patent [19]
Nishikata et al.

[11] Patent Number: 5,888,879
[45] Date of Patent: Mar. 30, 1999

[54] METHOD FOR EVALUATING MAKE-UP COSMETIC PRODUCT AND POWDER COMPOSITION

[75] Inventors: Kazuhiro Nishikata; Hirochika Nishimura, both of Yokohama, Japan

[73] Assignee: Pola Chemical Industries Inc., Shizuoka-ken, Japan

[21] Appl. No.: 874,160

[22] Filed: Jun. 13, 1997

[30] Foreign Application Priority Data

Jun. 13, 1996 [JP] Japan .................................... 8-174240
Sep. 12, 1996 [JP] Japan .................................... 8-263543

[51] Int. Cl.[6] ............................................. A61K 2/00
[52] U.S. Cl. .............................. 424/401; 424/59; 424/63; 424/78.03
[58] Field of Search ............................... 424/401, 78.03, 424/63, 59

[56] References Cited

U.S. PATENT DOCUMENTS

5,478,550 12/1995 Suzuki ....................................... 424/59

*Primary Examiner*—D. Gabrielle Brouillette
*Assistant Examiner*—D. Faulkner
*Attorney, Agent, or Firm*—Knobbe, Martens, Olson and Bears, LLP

[57] ABSTRACT

A make-up cosmetic product, which enhances the appearance of complexion, is evaluated by irradiating lights having a wavelength range of visible light onto a surface on which the make-up cosmetic product is applied, from at least two directions with different incident angles, measuring a plurality of spectra of reflected lights obtained from the irradiated lights, respectively, and comparing the spectrum patterns with each other. This clarifies the optical theory by which the skin looks beautiful and provides a method for evaluating a make-up cosmetic product making the skin look beautiful.

18 Claims, 4 Drawing Sheets

METHOD FOR EVALUATING MAKE-UP COSMETIC PRODUCT AND POWDER COMPOSITION

FIELD OF THE INVENTION

The present invention relates to a method for evaluating a make-up cosmetic product which is suitable for evaluation of foundation. The present invention also relates to a powder composition which is suitable for decoration such as make-up and is excellent in reproducing the texture of human skin.

BACKGROUND OF THE INVENTION

Every people, not limited to women, desire to look beautiful by others. In order to satisfy such a desire, various cosmetic products have been developed. Among them, basic cosmetic products which enhance the functions of the skin and make-up cosmetic products for decoration by means of optical effects can be exemplified. Among these cosmetic products, make-up cosmetic products are thought to be most contributing to making people look beautiful. Consumers mention this point as one of the largest motivations to use make-up cosmetic products.

However, methods of using make-up cosmetic products often depend on the experience and favor of each person. Thus, although scientific guidelines for a method for using a cosmetic product have recently been improved remarkably, it cannot be considered satisfactory at present.

Foundation, in particular, has been known to bear factors to make the skin look beautiful in addition to color and physical properties such as covering ability. For example, technique to make the skin look beautiful has been developed making use of optical effects such as defocusing make-up. We should say, however, that the optical effects and the mechanism to make people look beautiful have not been fully clarified.

That is to say, clarification of the theory to make people look beautiful and a development of a method for evaluating a make-up cosmetic product represented by foundation using the theory have been sought.

At the same time, it has been already known that color and design of costumes, etc., give different impression of beauty, etc., according to the shape and quality of the object to be decorated. For example, for this reason, when women with ordinary appearance wear a dress which looked beautiful when worn by a first-ranked model, the dress is not attractive as such. Also for this reason, color feeling or merits or demerits of the dress cannot be recognized by only watching the dress worn by a mannequin for a costume exhibition. Since even mannequins with a three-dimensional structure provides such a situation, two-dimensional photographs are so much the worse. It is natural that a lot of complaints stating that products shown in catalogues are quite different from real products are made.

As described above, as a significant factor of the cause giving different impression of beauty according to the objects to be decorated, the fact that the texture of human skin, the object, on mannequins and in two-dimensional photos is remarkably different from that of human. Although it is therefore required to reproduce the texture of actual human skin, it is not easy to create decoration (make-up) with the actual texture of human skin artificially.

Various efforts have been made so far to reproduce the texture of human skin. For example, three-dimensional images that utilize polarization to make people to see offset images, respectively, by the right eye and the left eye, and hologram have been attempted. However, they are only an attempt from viewpoints of two-dimension. At present, technique to make decoration with three-dimensional texture of the skin has not yet been accomplished, though it is required.

On the other hand, in the field of cosmetic products, although make-up to paint whole the face thickly, such as Kumadori for Kabuki, has been a main stream, beauty of sensitive feeling has recently taken a favorable turn. As make-up technique to realize such texture, defocusing make-up as mentioned above, etc., have been developed. With respect to these techniques, however, although the texture has been remarkably improved, problems in covering ability, etc., remain. That is, we await the development of make-up cosmetic products with excellent covering ability while possessing the ability to provide the texture of the skin.

SUMMARY OF THE INVENTION

The present invention has been made in view of the above circumstances, and therefore has an object of the invention to clarify the theory to make human skin look beautiful and to provide an objective method to evaluate a make-up cosmetic product without relying on experience and subjectivity.

It is another object of the present invention to clarify the optical theory to reproduce the texture of the skin and to provide a powder composition with the texture of the skin.

In view of the above circumstances, the present inventors have made an intensive study to clarify the optical mechanism to make human skin look beautiful. As a result, they found an optical effect derived from semi-transparency of the keratin layer as one of the factors enabling to reproduce the texture of human skin and make the skin look beautiful. The present invention has been made base on this finding.

Since the keratin layer is semi-transparent, most visible light incident at sharp angles close to 90 degrees with respect to the skin is reflected while visible light incident at shallow angles close to 0 degree is reflected with wavelength composition different from that of irradiated light due to absorption and scattering, etc. It was found that these sensitive differences in spectrum of reflected light greatly contributes to providing the texture of the skin and making the skin look beautiful as a factor other than color and physical properties such as masking ability.

It was also found that MAX-RAO values shown below can be suitably utilized as the optical characteristic values to express such a difference in spectrum of reflected light.

According to a first aspect of the present invention, there is provided a method for evaluating a make-up cosmetic product, which is featured by comprising the steps of: irradiating lights having a wavelength range of visible light onto a surface, on which the make-up cosmetic product is applied, from at least two directions with different incident angles with respect to the surface; measuring a plurality of spectra of reflected lights obtained from the irradiated lights, respectively; and comparing the spectrum patterns with each other.

In this method, the irradiated lights preferably includes a visible light having an incident angle of 10 to 60 degrees with respect to the surface and a visible light having an incident angle of 75 to 90 degrees with respect to the surface. Also, the irradiated lights preferably have a wavelength range of 400 to 700 nm. Further, the plurality of spectra of reflected lights are preferably measured independently, respectively. Still further, the irradiated lights are preferably irradiated from two directions with different incident angles with respect to the surface, more preferably the irradiated lights from two directions comprise a visible light having an incident angle of 10 to 60 degrees with respect to the surface and a visible light having an incident angle of 75 to 90 degrees with respect to the surface.

Furthermore, according to the first aspect of the present invention, the comparison process of the spectrum patterns preferably comprises the steps of: irradiating visible lights having a wavelength range of 400 to 700 nm from two directions with different incident angles with respect to the surface; measuring the spectra of two reflected lights obtained from the irradiated lights, respectively; calculating a MAX-RAO value from reflectance of the spectrum of each reflected light within the wavelength range according to the following equation (I):

$$MAX\text{-}RAO = [(B-A)/A]_{max} \quad (I)$$

wherein A represents reflectance of the reflected light from an irradiated light having a larger incident angle with respect to the surface; B represents reflectance of the reflected light from an irradiated light having a smaller incident angle with respect to the surface; and $[(B-A)/A]_{max}$ represents a maximum value of $(B-A)/A$ within the wavelength range; and comparing the spectrum patterns using the MAX-RAO value as an index.

The MAX-RAO value is the maximum value, within the measurement wavelength range, of [(reflectance of the reflected light from an irradiated light having a smaller incident angle with respect to the surface)−(reflectance of the reflected light from an irradiated light having a larger incident angle with respect to the surface)/(reflectance of the reflected light from an irradiated light having a larger incident angle with respect to the surface)] obtained at each wavelength by irradiating lights with a wavelength range of visible light from two directions with different incident angles with respect to the irradiated surface which is decorated with a make-up cosmetic product and measuring the spectra of the reflected lights.

The first aspect of the present invention is accomplished as a result of our finding that the MAX-RAO value thus obtained is served as an index to evaluate the degree of natural and beautiful looking of make-up by means of make-up cosmetic products.

According to the first aspect of the present invention, the make-up cosmetic product is preferably foundation.

According to a second aspect of the present invention, there is provided a powder composition, which is featured that the composition has a MAX-RAO' value of 3 to 8, which value is calculated from the reflectance of the spectra of two reflected lights obtained after irradiation of visible lights having a wavelength range of 400 to 700 nm to a smooth surface evenly packed with the powder composition at incident angles of 40 degrees and 85 degrees with respect to the surface according to the following equation (II):

$$MAX\text{-}RAO' = [(B'-A')/A']_{max} \quad (II)$$

wherein, A' represents the reflectance of the reflected light from an irradiated light having an incident angle of 85 degrees with respect to the surface; B' represents the reflectance of the reflected light from an irradiated light having an incident angle of 40 degrees with respect to the surface; and $[(B'-A')/A']_{max}$ represents a maximum value of $(B'-A')/A'$ within the wavelength range.

The second aspect of the present invention has been achieved by our finding that a powder composition with a MAX-RAO' value as a value indicating optical properties which is the maximum, within measurement wavelength range, of the values which are obtained by division of the difference in spectrum strength of reflected lights obtained by irradiation of visible lights to a smooth surface evenly packed with the powder composition at incident angles of 40 degrees and 85 degrees with respect to the surface by the spectrum strength of the reflected light from the irradiated light having a larger incident angle, of 3 to 8 is superior in providing the texture of the skin.

The composition is preferably comprised of inorganic powder selected from the group consisting of silica gel, cerite, talc, and sericite.

According to the second aspect of the present invention, the composition is preferably a cosmetic product or a paint.

DETAILED DESCRIPTION OF THE PREFERRED EMBODIMENTS

I. Method for Evaluating Make-up Cosmetic Product of the Present Invention

A method for evaluating a make-up cosmetic product of the present invention, in the most preferable embodiment, is carried out according to the following steps.

1) A visible light is irradiated from one direction to a surface undergoing make-up and a spectroscopic spectrum is determined for the reflected light thus obtained. Although the surface to undergo make-up is not particularly limited, it is preferable to measure after giving make-up to human skin, since suitable evaluation results are obtained.

2) A visible light is irradiated from a direction differing from that in the step (1) above, and a spectroscopic spectrum of the reflected light is determined in a similar manner.

At this instance, one of the incident angles of irradiated visible lights with respect to the surface with make-up is preferably 0 to 60 degrees, more preferably 10 to 60 degrees, further preferably 15 to 60 degrees, and another is preferably 75 to 90 degrees, more preferably 78 to 90 degrees, and further preferably 80 to 90 degrees. This is because since the reflected light from a light irradiated almost perpendicularly takes a form close to direct reflection and reflected light from a light irradiated almost horizontally is scattered or absorbed most to be quite different from the incident light, optical properties of the reflective surface can be grasped through a comparison of them.

3) The spectroscopic spectra of the two kinds of reflected light thus obtained are compared.

Figure 1:
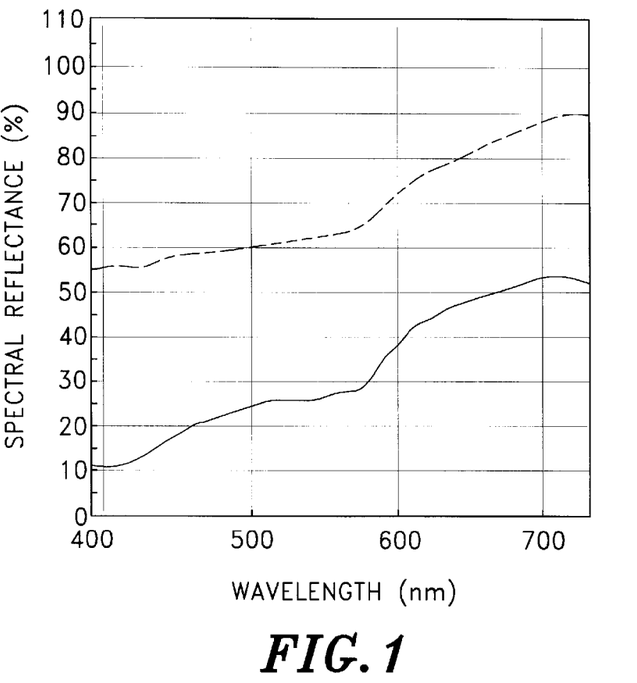
FIG. 1 represents spectroscopic spectra of the reflected lights obtained by irradiation of visible lights at incident angles of 85 degrees and 40 degrees to the untreated skin.
Figure 2:
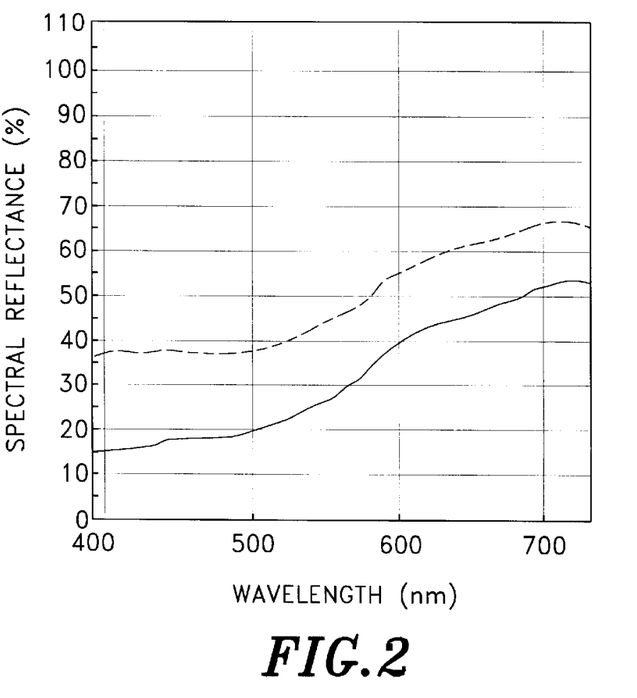
FIG. 2 represents spectroscopic spectra of the reflected lights obtained by irradiation of visible lights at incident angles of 85 degrees and 40 degrees to the skin undergoing make-up with mat foundation.
Figure 3:
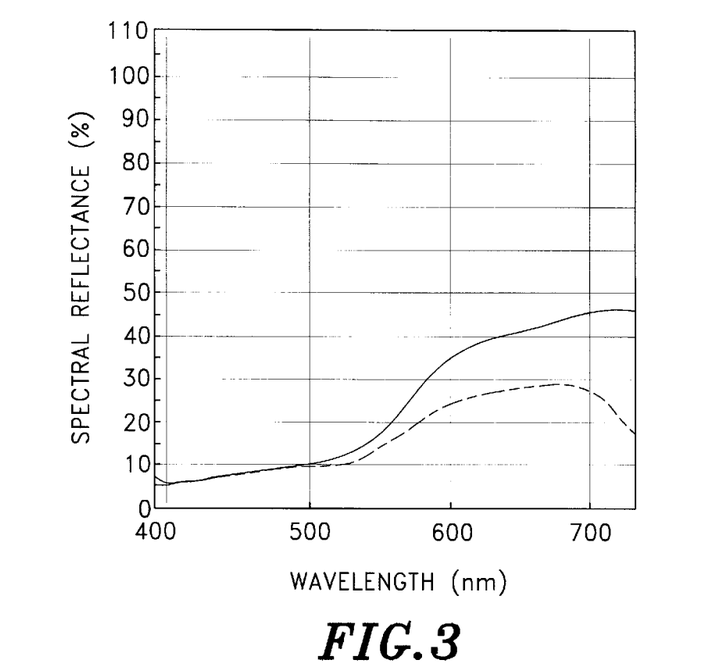
FIG. 3 represents spectroscopic spectra of the reflected lights obtained by irradiation of visible lights at incident angles of 85 degrees and 40 degrees to the standard skin color board.

FIGS. 1 to 3 show spectroscopic spectra of reflected lights determined after irradiation of lights with various wavelengths to the skin at incident angles of 40 degrees and 85 degrees. FIG. 1 shows spectroscopic spectra of normal skin (untreated skin of a panel whose skin is judged to be beautiful by gross examination); FIG. 2 shows spectroscopic spectra obtained after application of foundation which gives thick feeling (foundation of mat type) to the panel; and FIG. 3 shows spectroscopic spectra obtained using a standard skin color board. In the figures, a dotted line represents a spectrum obtained using a light of an incident angle of 85 degrees and a continuous line represents a spectrum obtained using a light of an incident angle of 40 degrees.

From FIGS. 1 to 3, a difference in spectrum pattern after application of foundation is situated in the middle of a difference in spectrum pattern for the skin without make-up and that for the standard skin color board. Therefore, it is clear that when a difference in spectrum pattern becomes close to that of the skin without make-up, finish with the texture of bare skin can be achieved, and that when it becomes close to that of the standard skin color board, mat finish is obtained. Consequently, the degree of natural and beautiful finish of make-up can be evaluated by comparing spectroscopic spectra of two kinds of reflected lights thus obtained.

The means for comparing spectrum pattern should not be limited so far that it can compare spectrum patterns qualitatively or quantitatively. However, it is convenient and preferable to obtain a MAX-RAO value determined as follows and to use it as an index.

According to a first aspect of the present invention, visible lights with a wavelength range of 400 to 700 are irradiated to the surface with make-up from two directions with different incident angles with respect to the surface; the spectra of the two kinds of reflected lights obtained from the irradiated lights are measured; and a MAX-RAO value, the maximum value within the measurement wavelength range, of [(reflectance of the reflected light of an irradiated light with a smaller incident angle with respect to the surface)−(reflectance of the reflected light of an irradiated light with a larger incident angle with respect to the surface)/ (reflectance of the reflected light of an irradiated light with a larger incident angle with respect to the surface)] is calculated; and the spectrum patterns are compared using the MAX-RAO value as an index.

Figure 5:
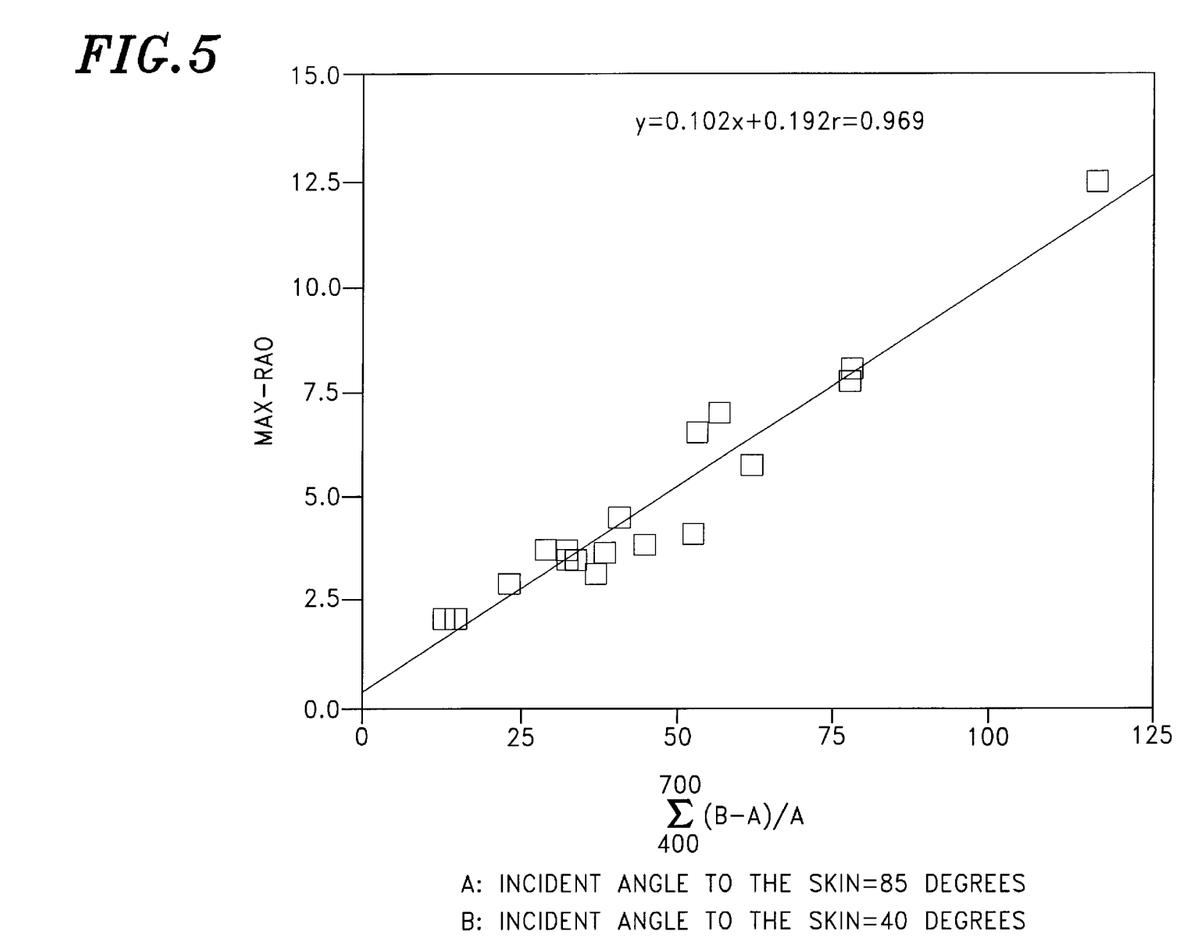
FIG. 5 shows the relationship between integrated values of spectroscopic differences and MAX-RAO values.

For a comparison of spectrum patterns of reflected lights of visible lights from these two directions, it is appropriate to use integrated values of the differences in spectral strength (spectral reflectance) within the measurement wavelength range. However, there is an excellent linear regression, as shown in FIG. 5, between the integrated values and MAX-RAO values. Therefore, the MAX-RAO value can be utilized as an index for a comparison of these spectroscopic spectra. In FIG. 5, plotted are integrated values of the difference in reflectance within the measurement wavelength of 400 to 700 nm, which is expressed by the following equation $$\sum_{400}^{700} [(B-A)/A] \qquad (III)$$

wherein, A represents reflectance of a reflected light of a visible light irradiated at an incident angle of 85 degrees; and B represents the reflectance of a reflected light of a visible light irradiated at an incident angle of 40 degrees, and which is calculated using the reflectance of spectroscopic spectrum of respective reflected lights obtained by irradiation of visible lights at incident angles of 40 degrees and 85 degrees and a MAX-RAO value calculated according to the above equation (I) using the same reflectance, for 20 panels optionally selected.

Figure 4:
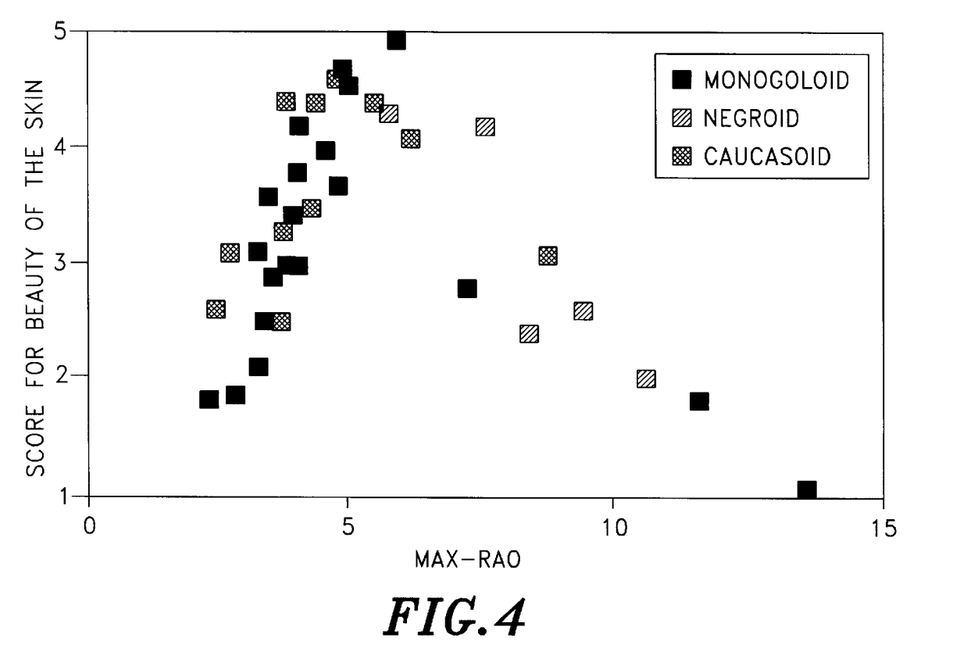
FIG. 4 shows the relationship between the beauty of bare skin and MAX-RAO values.

With respect to the relationship between the beauty of bare skin for various races and MAX-RAO values, it is judged to have excellent bare skin, regardless of race, when a MAX-RAO value ranges from 3 to 5, as shown in FIG. 4. In this case, the beauty of bare skin is evaluated by 5 specialized panels using a score 5 for "very beautiful" and a score 0 for "very unbeautiful" and average scores are used as representative values. The texture of the skin, smoothness of the skin, transparency of the skin, glossiness of the skin, smoothness of the skin surface, suppleness of the skin, and the absence of color unevenness are mentioned as factors for evaluation of the beauty of bare skin.

Therefore, it is possible to evaluate a make-up cosmetic product by measuring a MAX-RAO value and determining if the value is close to the value for standard beautiful skin. For example, when beautiful natural bare skin is used as a standard, a cosmetic product with a MAX-RAO value close to that of the standard bare skin is evaluated as a cosmetic product achieving natural make-up with the texture of bare skin. A cosmetic product with a small MAX-RAO value can be judged to be cosmetics which provide make-up of mat finish.

When incident angles of the irradiated visible lights are 85 degrees and 40 degrees, the MAX-RAO values of 4 to 7 can be mentioned to provide beautiful make-up with the texture of bare skin. These values change when incident angles change. Although this evaluation method can be most suitably applied to evaluation of foundation, it can also be utilized for evaluation of eye make-up, cheek color, and lip-color as a standard from unprecedented viewpoints.

More information can be obtained by analyzing visible light from more than two directions in a similar manner. However, such an analysis is rather complex to conduct, while relatively small information can be obtained. Thus, analysis using incident light from two directions is practical and preferable.

Light can be irradiated from various directions both individually and simultaneously. However, it is preferable to measure plurality of spectroscopic spectra independently respectively after individual irradiation, since this method provides a lot of merits, such as easy measurement, convenient operation, and easy analysis in a short period of time. Of course, in the analysis of reflected light, it is possible to use analysis of similarity of patterns, analysis of integrated values, and average of square of a difference as an index, without using MAX-RAO values. They also belong to the evaluation method of the present invention. It is preferable to make a comparison using MAX-RAO values in terms of convenience and appropriateness.

These spectral analysis can be conducted according to the conventional method using a commercially available spectrometer. The evaluation method of the present invention can be utilized in combination with other methods of evaluating a make-up cosmetic product such as covering strength index, a photographic sensitivity test and the like. Accuracy of evaluation can be enhanced in this case.

II. Powder Composition of the Present Invention

A powder composition of the second aspect of the present invention, when processed into an even plane, has a MAX-RAO value for the plane within a particular range and is suitable for cosmetic products and paints.

Particularly, the powder composition of the second aspect of the present invention is characterized in that a MAX-RAO' value among the MAX-RAO values mentioned above is used as an index. The MAX-RAO' value is the maximum value, within the measurement wavelength range, of [(reflectance of the reflected light of an irradiated light with an incident angle of 40 degrees with respect to the surface)−

(reflectance of the reflected light of an irradiated light with an incident angle of 85 degrees with respect to the surface)/(reflectance of the reflected light of an irradiated light with an incident angle of 85 degrees with respect to the surface)] at each wavelength calculated from reflectance of the two kinds of reflected lights obtained after irradiation of visible lights with a wavelength range of 400 to 700 nm to a smooth surface evenly packed with the powder composition from two directions with incident angles of 40 degrees and 85 degrees with respect to the surface; and that the MAX-RAO' value is 3 to 8.

The MAX-RAO' value is most preferably measured by the following steps:

1) To a powder composition evenly arranged in a plane, a visible light is irradiated at an angle of 40 degrees with respect to the plane of the powder composition and a spectroscopic spectrum of the reflected light thus obtained is determined.

2) A visible light is irradiated at an angle of 85 degrees to the same plane, and the spectroscopic spectrum of the reflected light is determined in a similar manner as the step (1).

3) The difference between the two spectroscopic spectra thus obtained at respective wavelengths is calculated and the value obtained according to the above equation (II) is designated as a MAX-RAO' value. This MAX-RAO' value is an index expressing the texture of the skin.

The powder composition of the second aspect of the present invention with the MAX-RAO' value of 3 to 8 can give the texture of the skin to the surface on which it is applied. The MAX-RAO' value preferable to provide the texture of the skin ranges from 3 to 8, more preferably 3 to 7, further preferably 4 to 6.

In order to arrange the MAX-RAO' value of the powder composition within the above range, adjustment can be carried out by altering a ratio of powder components.

In this case, an increase in a proportion of powder having a high MAX-RAO' value such as silica gel, titania sericite coated with silica-iron oxide and the like makes adjustment easier. In addition, if a composition with a high MAX-RAO' value is prepared in advance, adjustment is easily conducted by interpolation from ordinary products.

Powders which can be utilized in the powder composition according to the second aspect of the present invention can be any powder which is utilized in cosmetic products and paints, without particular limit. Silica gel, talc, sericite, bentonite, mica, titania mica, small sphere of acrylic resin, titan oxide, iron oxide, ultramarine blue, iron blue, carbon black, zinc oxide, chromium oxide, chromium hydroxide, alumina, calcium silicate, and calcium carbonate can be exemplified. Of course, these powder can undergo surface treatment with silicone, metal soap, etc.

According to the second aspect of the present invention, the powder composition preferably comprises inorganic powder selected from the group consisting of silica gel, cerite, talc, and sericite.

The powder composition of the second aspect of the present invention is suitable for cosmetic products and paints. When they are used for such applications, optional ingredients usually used in these formulations can be used for the composition of the present invention.

As for such optional components, hydrocarbons such as Vaseline, microcrystalline wax, esters such as jojoba oil and spermacetic wax, triglycerides such as beef tallow and olive oil, higher alcohols such as cetanol and oleic alcohol, fatty acids such as stearic acid and oleic acid, polyols such as glycerin and 1,3-butanediol, on-ionic surfactants, anionic surfactants, cationic surfactants, amphoteric surfactants, ethanol, thickeners such as carbopol, preservatives, UV absorbents, anti-oxidants, pigments, and powder can be exemplified for cosmetic products; and coat forming agents, binders, dispersants, plasticizers, anti-rusting agents, and solvents can be mentioned for paints.

The powder composition of the second aspect of the present invention is preferably used in cosmetic products, particularly in make-up cosmetic products.

EXAMPLE

The present invention will be further illustrated below by referring examples, but it is obvious that the present invention is not restricted by the examples.

[Example 1]

Ten female panels were optionally selected and underwent make-up using two types of foundation giving different finish, that is, mat-type foundation (Foundation 1) and transparent-type foundation (Foundation 2). Visible light was irradiated at 85 degrees and 40 degrees with respect to their bare skin and skin with make-up using the above-mentioned foundation. The reflected light was analyzed by a spectrophotometer (U-3500 Spectrophotometer, Hitachi, Ltd.). Then, [(reflectance of reflected light from visible light with an incident angle of 40 degrees)–(reflectance of reflected light from visible light with an incident angle of 85 degrees)/(reflectance of reflected light from visible light with an incident angle of 85 degrees)] was calculated and its maximum value, the MAX-RAO value, was obtained.

At the same time, five specialized panels evaluated the finish from the viewpoints of transparency and naturalness. Evaluation was made for transparency using score 0 for "looks very thick like a skin-color tile" and score 10 for "looks like the skin of a panel herself"; and for naturalness using score 0 for "looks like a skin-color tile" and score 10 for "looks like the skin of a panel herself".

Figure 6:
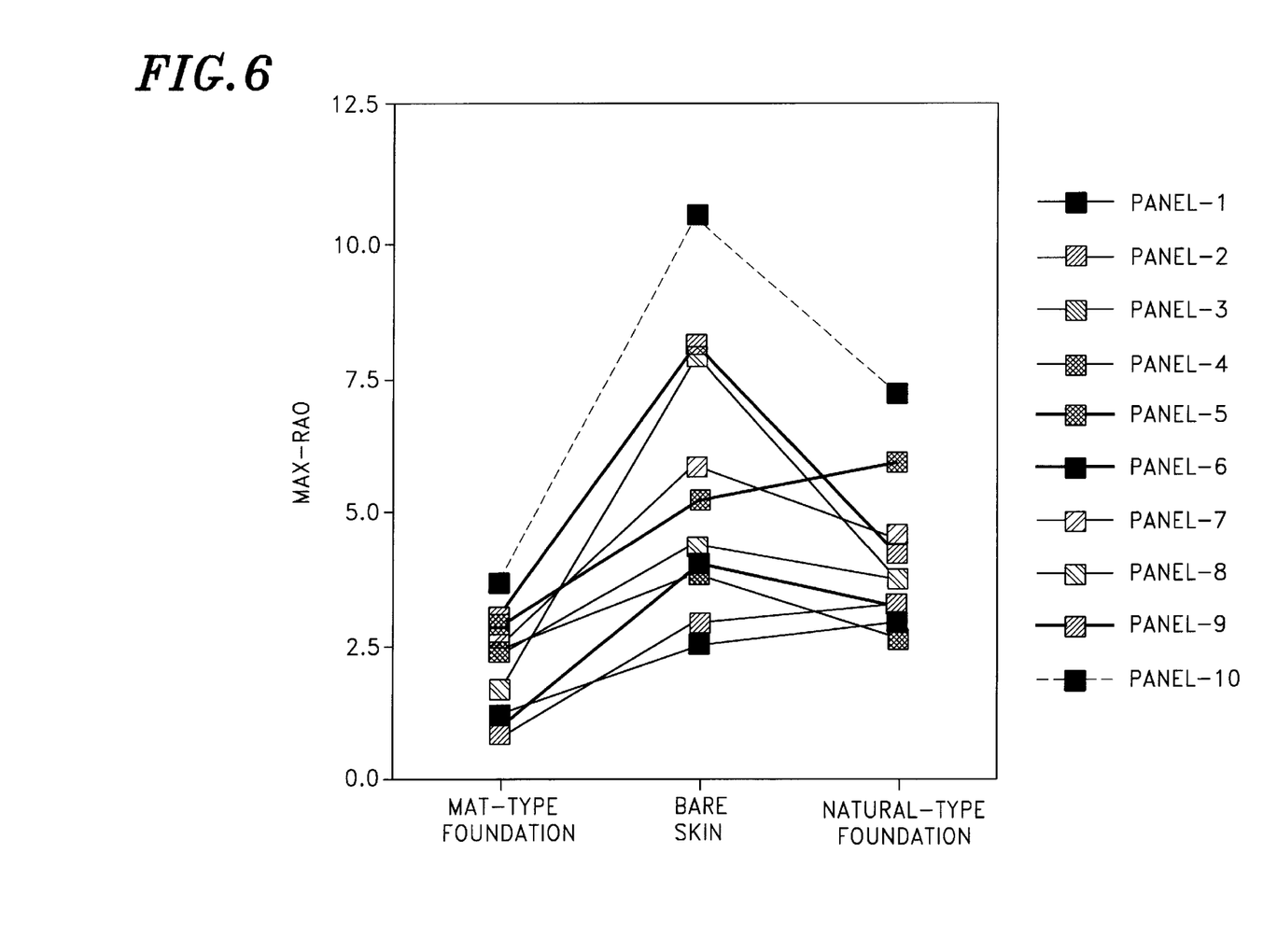
FIG. 6 shows the changes in MAX-RAO values for intact skin and when two kinds of foundation are applied.

FIG. 6 shows the finish for each foundation and the changes in MAX-RAO value of bare skin. The average scores for transparency were 5.8 for Foundation 1 and 8.4 for Foundation 2. The average score for natural make-up were 4.9 for Foundation 1 and 8.8 for Foundation 2. There results clearly indicate that make-up achieving a MAX-ROA value close to that of bare skin gives beautiful make-up with the feeling of bare skin according to the evaluation of other persons.

[Example 2]

Evaluation was made also on cheek-color using one panel as in Example 1. Mat-type cheek-color (Cheek-color 1) and cheek-color giving natural feeling (Cheek-color 2) were used. The MAX-RAO value for Cheek-color 1 was 1.8 and that of Cheek-color 2 was 3.1. The MAX-RAO value for bare skin was 2.8. The scores for transparency were 4.9 for Cheek-color 1 and 7.6 for Cheek-color 2; and those for natural make-up were 5.3 for Cheek-color 1 and 8.1 for Cheek-color 2. There results indicate that make-up achieving a MAX-ROA value close to that of bare skin gives beautiful make-up with the feeling of bare skin according to the evaluation of other persons.

[Example 3]

Foundation was prepared according to the formulation shown below. The components shown in (A) were weighed and placed in a Henschel mixer and stirred thoroughly by rotation at low speed. The resultant was broken up cohesions by a pulverizer equipped with a screen with holes of 0.7 mm, and then returned to the Henschel mixer again, to which components in (B) were dropped with stirring by rotation at low speed to coat. After that, the resultant was mixed evenly at high rotation speed, broken up cohesions with a pulverizer equipped with a 1.0 mm herringbone screen, packed in a metal dish, and subjected to pressurized molding to obtain foundation.

The MAX-RAO value measured for the surface of the product of pressurized molding was 3.8. It is clear that MAX-RAO value can be adjusted to 3 to 6 using a combination of only conventional raw materials without using special raw materials. It is also clear that the value can be increased by adding some titania mica coated with silica-iron oxide.

|  | (Unit: part by weight) |
|---|---|
| (A) | |
| Titania mica coated with silica-iron oxide | 16 |
| Mica treated with silicone | 14 |
| Sericite treated with silicone | 15 |
| Polymethysilsesquioxane | 4 |
| Titania mica treated with silicone | 18 |
| Titanium dioxide treated with silicone | 12 |
| Talc treated with silicone | 3 |
| Yellow iron oxide treated with silicone | 2 |
| Red iron oxide treated with silicone | 1 |
| Nylon powder | 5 |
| (B) | |
| Dimethicone | 5 |
| Squalane | 5 |

[Example 4]

Foundation was prepared according to the formulation shown below. The components shown in (A) were weighed and placed in a Henschel mixer and stirred thoroughly by rotation at low speed. The resultant was broken up cohesions by a pulverizer equipped with a screen with holes of 0.7 mm. It was then returned to the Henschel mixer, to which components in (B) were dropped with stirring by rotation at low speed to coat After that, the resultant was mixed evenly at high rotation speed, broken up cohesions with a pulverizer equipped with a 1.0 mm herringbone screen, packed in a metal dish, and subjected to pressurized molding to obtain foundation.

The MAX-RAO value measured for the surface of the product of pressurized molding was 4.1. It is clear that MAX-RAO value can be adjusted to 3 to 6 using combination of conventional raw materials only without using special raw material. It is also clear that the value can be increased by adding some titania mica coated with silica-iron oxide.

|  | (Unit: part by weight) |
|---|---|
| (A) | |
| Red iron oxide treated with silicone | 1 |
| Yellow iron oxide treated with silicone | 0.9 |
| Marine blue treated with silicone | 0.1 |
| Titanium dioxide treated with silicone | 28 |
| Titania mica treated with silicone | 6 |
| Titania sericite coated with silica-iron oxide | 16 |
| Titanium dioxide baked with iron treated with silicone | 1 |
| Sericite treated with silicone | 30 |
| Titania sericite treated with silicone | 5 |
| (B) | |
| Dimethicone | 12 |

[Example 5]

Foundation was prepared according to the formulation shown below. The components shown in (A) were weighed and placed in a Henschel mixer and stirred thoroughly by rotation at low speed. The resultant was broken up cohesions by a pulverizer equipped with a screen with holes of 0.7 mm. It was then returned to the Henschel mixer, to which components in (B) were dropped with stirring by rotation at low speed to coat. After that, the resultant was mixed evenly at high rotation speed, broken up cohesions with a pulverizer equipped with a 1.0 mm herringbone screen, packed in a metal dish, and subjected to pressurized molding to obtain foundation.

The MAX-RAO value measured for the surface of the product of pressurized molding was 3.1 It is clear that MAX-RAO value can be adjusted to 3 to 6 using a combination of conventional raw materials only without using special raw materials. It is also clear that the value can be increased by adding some titania mica coated with silica-iron oxide.

|  | (Unit: part by weight) |
|---|---|
| (A) | |
| Titania mica coated with silica-iron oxide | 10 |
| Mica treated with silicone | 16 |
| Sericite treated with silicone | 19 |
| Polymethylsilsesquioxane | 4 |
| Titania mica treated with silicone | 18 |
| Titanium dioxide treated with silicone | 12 |
| Talc treated with silicone | 3 |
| Yellow iron oxide treated with silicone | 2 |
| Red iron oxide treated with silicone | 1 |
| Nylon powder | 5 |
| (B) | |
| Dimethicone | 5 |
| Squalane | 5 |

[Example 6]

Foundation was prepared according to the formulation shown below. The components shown in (A) were weighed and placed in a Henschel mixer and stirred thoroughly by rotation at low speed. The resultant was broken up cohesions by a pulverizer equipped with a screen with holes of 0.7 mm. It was then returned to the Henschel mixer, to which components in (B) were dropped with stirring by rotation at low speed to coat After that, the resultant was mixed evenly at high rotation speed, broken up cohesions with a pulverizer equipped with a 1.0 mm herringbone screen, packed in a metal dish, and subjected to pressurized molding to obtain foundation. The MAX-RAO value measured for the surface of the product of pressurized molding was 3.3.

It becomes clear that a MAX-RAO value can be adjusted to 3 to 6 using a combination of conventional raw materials only without using special raw materials. It is also clear that the value can be increased by adding some titania mica coated with silica-iron oxide. In addition, it is clear that addition of silica gel has a similar effect.

|  | (Unit: Part by weight) |
|---|---|
| (A) | |
| Titania mica coated with silica-iron oxide | 10 |
| Mica treated with silicone | 14 |
| Sericite treated with silicone | 15 |
| Fumed silica gel | 6 |
| Polymethylsilsesquioxane | 4 |
| Titania mica treated with silicone | 18 |
| Titanium dioxide treated with silicone | 12 |

-continued

| | (Unit: Part by weight) |
|---|---|
| Talc treated with silicone | 3 |
| Yellow iron oxide treated with silicone | 2 |
| Red iron oxide treated with silicone | 1 |
| Nylon powder | 5 |
| (B) | |
| Dimethicone | 5 |
| Squalane | 5 |

[Reference Example]

Foundation was prepared according to the formulation shown below. The components shown in (A) were weighed and placed in a Henschel mixer and stirred thoroughly by rotation at low speed. The resultant was broken up cohesions by a pulverizer equipped with a screen with holes of 0.7 mm. It was then returned to the Henschel mixer, to which components in (B) were dropped with stirring by rotation at low speed to coat After that, the resultant was mixed evenly at high rotation speed, broken up cohesions with a pulverizer equipped with a 1.0 mm herringbone screen, packed in a metal dish, and subjected to pressurized molding to obtain foundation.

The MAX-RAO value measured for the surface of the product of pressurized molding was 2.7. The result indicates that conventional foundation has a low MAX-RAO value.

| | (Unit: Part by weight) |
|---|---|
| (A) | |
| Titan dioxide treated with silicone | 12.5 |
| Red iron oxide treated with silicone | 1 |
| Yellow iron oxide treated with silicone | 2 |
| Mica treated with silicone | 37 |
| Talc treated with silicone | 30 |
| Sericite treated with silicone | 11 |
| Cellulose powder | 3 |
| Polymethyl methacrylate | 3.5 |
| (B) | |
| Squalane | 6 |
| Microcrystalline wax | 0.5 |
| Octyldodecyl lactate | 2 |
| Dimethicone | 2.5 |

[Example 7]
<Evaluation Test>

Models underwent make-up using the foundations prepared in Examples 3 to 6 and Reference Example and 5 specialized cosmeticians were requested to evaluate make-up with respect to the following items according to the criteria shown below. The results are shown in Table 1 using average scores. The results show that when a MAX-RAO value exceeds 3, an effect of masking troubles, etc. is enhanced and natural make-up can be obtained. It is also indicated that foundation with a MAX-RAO value exceeding 4 has a remarkable cosmetic effect.
(Evaluation items and Criteria for Scores)
(1) If the foundation can mask troubles: Score 5: Can mask well; Score 4: Can make relatively well; Score 3: Can mask; Score 2: Slightly problematic in masking; Score 1: Problematic in masking; and Score 0: Cannot mask at all.
(2) If the make-up looks natural: Score 5: Looks very natural; Score 4: Looks relatively natural; Score 3: Looks natural; Score 2: Looks slightly unnatural; Score 1: Looks considerably unnatural; and Score 0: Looks completely unnatural (3) If the make-up is beautiful: Score 5: Very beautiful; Score 4: Satisfactorily beautiful; Score 3: Beautiful; Score 2: Slightly problematic; Score 1: Problematic; and Score 0: Out of question

TABLE 1

| Evaluation items | Example 3 | Example 4 | Example 5 | Example 6 | Reference Example |
|---|---|---|---|---|---|
| Trouble masking | 4.8 | 4.8 | 4.8 | 4.8 | 3.6 |
| Naturality of make-up | 4.6 | 4.8 | 4.0 | 4.4 | 2.6 |
| Beauty of make-up | 4.5 | 4.8 | 4.2 | 4.4 | 4.2 |

[Example 8]

A powder composition was prepared using the formulation shown below. The components were mixed using a Henschel mixer and broken up cohesions with pulverizer equipped with 0.7 mm holes to obtain a powder composition. The MAX-RAO value was 4.3. The composition thus obtained was adhered to the surface of a mannequin doll using adhesives. As a result, the mannequin doll looked like human. The result indicates that the powder composition of the present invention is useful as a paint.

| Components of Formulation | (Unit: Part by weight) |
|---|---|
| Red iron oxide treated with silicone | 1.3 |
| Yellow iron oxide treated with silicone | 1 |
| Marine blue treated with silicone | 0.1 |
| Titanium dioxide treated with silicone | 31.8 |
| Titania mica treated with silicone | 6.8 |
| Titania sericite treated with silica-iron oxide | 18.2 |
| Titanium dioxide baked with iron and treated with silicone | 1.1 |
| Sericite treated with silicone | 34 |
| Titania sericite treated with silicone | 5.7 |

The present invention can clarify the optical theory to make the texture of the skin appear and the skin look beautiful and provide a method for evaluating a make-up cosmetic product making the skin look beautiful and the powder composition giving the texture of the skin.

What is claimed is:

1. A method for evaluating a make-up cosmetic product comprising the steps of:
   irradiating lights having a wavelength range of visible light onto a surface, on which said make-up cosmetic product is applied, from at least two directions with different incident angles with respect to said surface;
   measuring a plurality of spectra of reflected lights obtained from the irradiated lights, respectively; and
   comparing the spectrum patterns of said spectra with each other.

2. A method for evaluating a make-up cosmetic product as claimed in claim 1, wherein said irradiated lights include a visible light having an incident angle of 10 to 60 degrees with respect to said surface and a visible light having an incident angle of 75 to 90 degrees with respect to said surface.

3. A method for evaluating a make-up cosmetic product as claimed in claim 1, wherein said irradiated lights have a wavelength range of 400 to 700 nm.

4. A method for evaluating a make-up cosmetic product as claimed in claim 1, wherein said plurality of spectra of reflected lights are measured independently, respectively.

5. A method for evaluating a make-up cosmetic product as claimed in claim 1, wherein said irradiated lights are irradiated from two directions with different incident angles with respect to said surface.

6. A method for evaluating a make-up cosmetic product as claimed in claim 5, wherein said irradiated lights comprise a visible light having an incident angle of 10 to 60 degrees with respect to said surface and a visible light having an incident angle of 75 to 90 degrees with respect to said surface.

7. A method for evaluating a make-up cosmetic product as claimed in claim 1, wherein, said comparison process comprises the steps of:
   irradiating visible lights having a wavelength range of 400 to 700 nm from two directions with different incident angles with respect to said surface;
   measuring the spectra of two reflected lights obtained from said irradiated lights, respectively;
   calculating a MAX-RAO value from reflectance of the spectrum of each reflected light within said wavelength range according to the following equation (I):

$$MAX\text{-}RAO = [(B-A)/A]_{max} \quad (I)$$

wherein A represents reflectance of the reflected light from irradiated light having a larger incident angle with respect to said surface; B represents reflectance of the reflected light from irradiated light having a smaller incident angle with respect to said surface; and $[(B-A)/A]_{max}$ represents a maximum value of $(B-A)/A$ within said wavelength range; and
   comparing said spectrum pattern using said MAX-RAO 5 value as an index.

8. A method for evaluating a make-up cosmetic product as claimed in claim 1, wherein said make-up cosmetic product is foundation.

9. A powder composition, characterized in that said composition has a MAX-RAO' value of 3 to 8, which value is calculated from the reflectance of the spectra of two reflected light obtained after irradiation of visible light having a wavelength range of 400 to 700 nm with respect to a smooth surface evenly packed with said powder composition at incident angles of 40 degrees and 85 degrees with respect to said surface according to the following equation (II):

$$MAX\text{-}RAO' = [(B'-A')/A']_{max} \quad (II)$$

wherein, A' represents the reflectance of the reflected light from an irradiated light having an incident angle of 85 degrees with respect to said surface; B' represents the reflectance of the reflected light from an irradiated light having an incident angle of 40 degrees with respect to said surface; and $[(B'-A')/A']_{max}$ represents a maximum value of (B'-A")/A' within said wavelength range.

10. A powder composition as claimed in claim 9, wherein said composition comprises inorganic powder selected from the group consisting of silica gel, cerite, talc, and sericite.

11. A powder composition as claimed in claim 10, wherein said composition is used for a cosmetic product or a paint.

12. A method for enhancing the appearance of complexion, comprising the step of applying a powder composition onto a surface of skin in an amount effective to enhance the appearance of the complexion of the skin, said powder composition having a MAX-RAO' value of 3 to 8, which value is calculated from the reflectance of the spectra of two reflected light obtained after irradiation of visible light having a wavelength range of 400 to 700 nm with respect to a smooth surface evenly packed with said powder composition at incident angles of 40 degrees and 85 degrees with respect to said surface according to the following equation (II):

$$MAX\text{-}RAO' = [(B'-A')/A']_{max}$$

wherein A' represents the reflectance of the reflected light from an irradiated light having an incident angle of 85 degrees with respect to said surface: B' represents the reflectance of the reflected light from an irradiated light having an incident angle of 40 degrees with respect to said surface: and $[(B'-A')/A']_{max}$ represents a maximum value of (B'-A')/A' within said wavelength range.

13. A method for enhancing the appearance of complexion, comprising the steps of:
   selecting a make-up cosmetic based on the evaluation according to claim 1; and
   applying said make-up cosmetic onto a surface of skin in an amount effective to enhance the appearance of the complexion of the skin.

14. A method for evaluating a make-up cosmetic product as claimed in claim 1, further comprising the step of correlating the appearance of the make-up cosmetic product-applied surface with the compared spectrum patterns.

15. A method for formulating a make-up cosmetic product, comprising the steps of:
   preparing a make-up cosmetic product having a formula;
   shaping said product to form a flat surface;
   irradiating visible light having a wavelength range of 400 to 700 nm onto the flat surface, at a low incident angle and at a high incident angle with respect to the flat surface wherein the low incident angle is in the range of 10–60 degrees and the high incident angle is in the range of 75–90 degrees;
   measuring the spectra of light reflected by the flat surface, said reflected light obtained from the irradiated light at the respective incident angles;
   comparing the spectra obtained at the low incident angle and those at the high incident angle to calculate a difference in spectral reflectance therebetween; and
   changing the formula of the product until the calculated difference falls within a predetermined range if the calculated difference does not fall within the predetermined range.

16. The method according to claim 15, wherein, in the comparing step, an integrated value of a difference in spectral reflectance at each wavelength is calculated.

17. The method according to claim 15, wherein, in the comparing step, a MAX-RAO value is calculated using the equation $$MAX\text{-}RAO = [(B-A)/A]_{max}$$

wherein A is a spectral reflectance of the reflected light from the irradiated light at the high incident angle; B is a spectral reflectance of the reflected light from the irradiated light at the low incident angle; $[(B-A)/A]_{max}$ is a maximum value of $(B-A)/A$ within the wavelength range.

18. The method according to claim 17, wherein the predetermined range of the MAX-RAO value is 3 to 8.

* * * * *